United States Patent
He et al.

(10) Patent No.: US 6,482,844 B1
(45) Date of Patent: Nov. 19, 2002

(54) 1-BENZYLIMIDAZOLE DERIVATIVES

(75) Inventors: Xiao-Shu He, Branford, CT (US); Xiaoyan Zhang, Belle Meade, NJ (US); He Zhao, Branford, CT (US); Robert DeSimone, Durham, CT (US); Andrew Thurkauf, Danbury, CT (US)

(73) Assignee: Neurogen Corporation, Branford, CT (US)

( * ) Notice: Subject to any disclaimer, the term of this patent is extended or adjusted under 35 U.S.C. 154(b) by 26 days.

(21) Appl. No.: 09/827,565

(22) Filed: Apr. 6, 2001

Related U.S. Application Data

(60) Provisional application No. 60/195,537, filed on Apr. 7, 2000.

(51) Int. Cl.[7] .................... A61K 31/415; C07D 233/54
(52) U.S. Cl. .................................... 514/399; 548/338.1
(58) Field of Search ..................... 514/399; 548/338.1

(56) References Cited

U.S. PATENT DOCUMENTS

| | | | | |
|---|---|---|---|---|
| 6,258,834 B1 | * | 7/2001 | Hayashi et al. | 514/400 |
| 6,271,241 B1 | * | 8/2001 | DeSimone et al. | 514/303 |
| 6,297,268 B1 | * | 10/2001 | Evans et al. | 514/399 |
| 6,358,949 B1 | * | 3/2002 | DeSimone et al. | 514/234.5 |

* cited by examiner

*Primary Examiner*—Deborah C. Lambkin

(57) ABSTRACT

Provided are compounds (and pharmaceutically acceptable non-toxic salt of such compounds) of the formula:

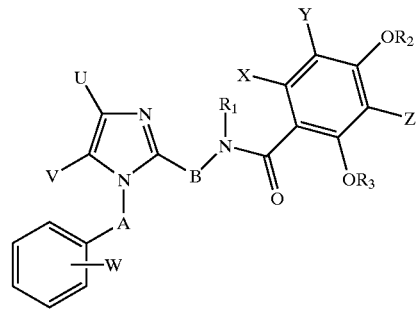

in which A and B are $C_1$–$C_3$ alkylene; $R_1$ is $C_1$–$C_6$ alkyl; $R_2$ and $R_3$ are hydrogen or $C_1$–$C_6$ alkyl; U and V are $C_1$–$C_6$ alkyl or halogen; X, Y and Z are hydrogen, $C_1$–$C_6$ alkyl, trifluoromethyl, $C_1$–$C_6$ alkoxy, trifluoromethoxy, halogen, or cyano; and W represents up to three substituents which are $C_1$–$C_6$ alkyl, trifluoromethyl, $C_1$–$C_6$ alkoxy, trifluoromethoxy, halogen, hydroxy, amino, or cyano. These compounds act as modulators of blood glucose levels and are useful for the treatment of diabetes, eating disorders, and obesity. Pharmaceutical compositions and methods of use of the compounds as pharmaceutical agents are also provided.

22 Claims, No Drawings

1-BENZYLIMIDAZOLE DERIVATIVES

This application claims priority from U.S. Provisional Application No. 60/195,537, filed Apr. 7, 2000, which is hereby incorporated by reference in its entirety.

BACKGROUND OF THE INVENTION

1. Field of the Invention

This invention relates to 1-benzylimidazole derivatives, and more specifically, to the use of such compounds as pharmaceutical agents, e.g., as modulators of blood glucose levels. This invention also relates to pharmaceutical compositions comprising such compounds and to the use of such compounds in treating a variety of disorders associated with feeding and food metabolism. Additionally, this invention relates to the use such compounds as probes for the localization of cellular receptors that are involved in the modulation of blood glucose levels.

2. Description of the Related Art

Diabetes mellitus is a chronic syndrome of impaired carbohydrate and fat metabolism resulting from insufficient insulin secretion and/or target tissue insulin resistance. It occurs in two major forms: insulin-dependent diabetes mellitus (IDDM, Type 1) and non-insulin-dependent diabetes mellitus (NIDDM, Type 2). These forms differ in their etiology, age of onset and treatment. Type 1 is often characterized by onset during childhood and the patients typically become fully dependent upon exogenous insulin to sustain life. The disorder is associated with a lack of insulin production by the pancreatic Islets of Langerhans. The disease is generally marked by a drastic reduction in the number of insulin secreting islet beta cells.

NIDDM usually appears later in life (typically ages 40–60) and is often associated with obesity. Patients with NIDDM show normal basal levels of insulin but display an abnormal insulin secretion response (delayed or reduced) to a glucose load. As the disease progresses, insulin target tissues show signs of diminished response to insulin (insulin resistance). Effective treatment of the disorder is usually obtained by dietary control, with or without the use of oral hypoglycemic drugs. Sulphonylureas are a class of hypoglycemic compounds used in the treatment of NIDDM. These drugs exert their action by causing insulin to be released from intracellular stores. Care must be taken in the administration of these agents in order to not induce severe hypoglycemia due to excessive insulin release. In addition, overdose may deplete insulin stores to a point requiring administration of exogenous insulin.

The discovery that glucose administered via the gastrointestinal tract provides greater stimulation of insulin release than a comparable glucose challenge given intravenously led to the identification of certain gut secreted 'incretin' hormones which augment glucose stimulated insulin secretion, and the identification of specific cell surface receptors that modulate the effects of such incretin hormones. Glucagon-like Peptide-1 (7-36)-amide (GLP-1) is one such incretin hormone that is secreted from gastrointestinal L cells in response to food intake and increases insulin secretion from pancreatic beta cells. GLP-1 is believed to exert its actions via binding to a G-protein-linked receptor expressed in islet β-cells.

Unlike the sulphonylureas, the effects of GLP-1 are dependent upon plasma glucose concentration; the insulinotropic effects of GLP-1 are abolished at low plasma glucose levels. In addition to its stimulation of insulin secretion, GLP-1 also increases insulin synthesis, inhibits glucagon secretion, and delays gastric emptying. This combination of actions gives GLP-1 unique potential therapeutic advantages over other agents presently used to treat non-insulin dependent diabetes mellitus. In a clinical trial of patients with NIDDM it was found that subcutaneous administration of GLP-1 could normalize postprandial glucose levels. Drugs that mimic the action of GLP-1, i.e. stimulate insulin secretion from pancreatic β-cells, but only at higher than normal blood glucose levels, are particularly desirable for use in the treatment of NIDDM. Such drugs may work by modulating the signal-transducing activity of the GLP-1 receptor.

In vitro experiments that monitor the interaction of the compound with GLP-1 receptors may also be used to reliably predict the effects of a compound on blood glucose levels. In one such experiment the interaction of compounds with GLP-1 receptors, expressed either recombinantly or naturally in high abundance in certain cell lines, may be determined by a cell-based luciferase screen or by binding experiments measuring competition binding, e.g., the competition of a test compound with a labeled GLP-1 ligand such as GLP-1 or GLP(7-36) peptide.

Receptors that are coupled to the $G_{s\alpha}$ stimulatory G-protein subunit transduce intracellular signals via the adenylate cyclase pathway. Stimulation of these receptors with an agonist typically results in an elevation of cytoplasmic cAMP levels, which can trigger the subsequent transcription of a variety of genes, generally those with promoters containing binding sites (CAMP responsive elements—CRES) for the transcription factor, CREB (CRE binding protein).

Receptor modulation may be measured via quantitation of transcriptional activation of a firefly luciferase reporter gene. Such an assay may use a Chinese hamster ovary cell line (CHO-K1) stably transfected with a GLP-1 receptor (a $G_{s\alpha}$ coupled receptor) expression plasmid and a luciferase reporter plasmid, wherein luciferase expression is under the transcriptional control of multiple CREs. In these cell lines, the GLP1 agonist GLP(7-36) peptide stimulates luciferase expression in a dose dependent manner with a potency ($EC_{50}$~20 pM) similar to the data reported by Gromada et al. (1995) *FEBS Lett.* 373: 182–186.

Compounds may be screened by seeding 15,000 cells per well in opaque multi-well plates. Cells are then incubated overnight in a tissue culture incubator. Compounds are dispensed to a final concentration of 4 uM in 1% DMSO. After 6 hours of incubation, cells are assayed for luciferase activity, which is measured in a luminometer.

In clinical studies GLP-1 has been shown to reduce appetite and increase satiety in both normal weight and obese subjects. Thus, drugs that modulate the activity of the GLP-1 receptor may be useful for the treatment of obesity and eating disorders.

SUMMARY OF THE INVENTION

This invention provides novel compounds of Formula I, below, as well as non-toxic pharmaceutically acceptable salts thereof. As used herein and in the claims, the terms "compound" and "salt" encompass anhydrous forms as well as hydrates. The invention also provides novel compounds of Formula I that bind specifically, and preferably with high affinity, to specific cellular receptors. Preferably the receptors are cell surface receptors, more preferably G-protein coupled receptors, yet more preferably the receptors are Secretin-like receptors, highly preferred receptors are GLP receptors, most preferably the receptors are GLP-1 receptors. Such compounds are useful in the treatment of diabetes, especially non-insulin-dependent diabetes mellitus (Type 2 diabetes), and in the treatment of obesity and eating disorders. Preferred compounds of the invention are non-toxic.

The invention further comprises methods of treating patients suffering from diabetes, especially non-insulin-dependent diabetes mellitus (Type 2 diabetes), obesity or eating disorders by administering to a patient in need of such treatment an effective amount of a compound of the invention. The patient may be a human or another, preferably mammalian, animal. Treatment of humans, domesticated companion animals (pets) or livestock animals suffering from these disorders with an effective amount of a compound of the invention is also encompassed by the invention. For veterinary applications, a wide variety of subjects will be suitable, e.g. livestock such as cattle, sheep, goats, cows, swine and the like; and domesticated animals particularly pets such as dogs and cats. For diagnostic or research applications, a wide variety of mammals will be suitable subjects including rodents (e.g. mice, rats, hamsters), rabbits, primates, and swine such as outbred or inbred pigs and the like. Additionally, for in vitro applications, such as in vitro diagnostic and research applications, body fluids and cell samples of the above subjects will be suitable for use, such as mammalian, particularly primate such as human, blood, urine or tissue samples, or blood urine or tissue samples of the animals mentioned for veterinary applications.

In a separate aspect, this invention provides compounds that are useful as probes for the detection and localization of specific receptors including GLP-1 Receptors. Preferably these receptors modulate blood glucose levels. Such receptors are preferably so localized in tissue samples, for example tissue sections. Such probes are also useful for measuring levels of such receptors expressed in tissue samples or cell membrane preparations of tissue samples and for detecting and localizing receptors in living patients (e.g., via PET scanning).

The invention also comprises a method for altering the signal-transducing activity of a cell surface GLP1 receptor, said method comprising exposing cells expressing such a receptor to an amount of a compound of the Formula I, below that is sufficient to effect either directly or indirectly detectable changes in receptor signal transduction.

The invention also provides pharmaceutical compositions comprising compounds of Formula I, including packaged pharmaceutical compositions. Packaged pharmaceutical compositions may include a container and instructions for using the composition to treat a patient in need thereof (such instructions preferably provided as indicia on a label incorporated in or on the package. Particularly, the invention includes packaged pharmaceutical compositions that include a container and instructions for using the composition to treat a patient suffering from diabetes, obesity or one or more eating disorders. As used herein and in the claims, obesity is not considered an eating disorder, but may represent the consequence of such a disorder.

Accordingly, a broad embodiment of the invention is directed to compounds of Formula I:

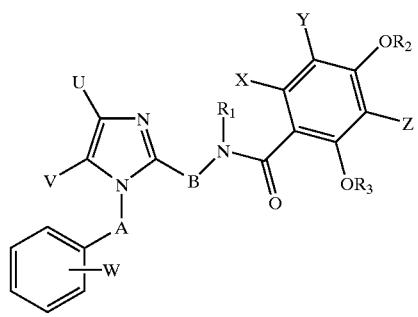

Formula I or the pharmaceutically acceptable salts thereof, wherein:
A and B are independently $C_1$–$C_3$ alkylene;
$R_1$ is $C_1$–$C_6$ alkyl;
$R_2$ and $R_3$ are the same or different and represent hydrogen or $C_1$–$C_6$ alkyl;
U and V are the same or different and represent $C_1$–$C_6$ alkyl or halogen;
X, Y and Z are the same or different and represent hydrogen, $C_1$–$C_6$ alkyl, trifluoromethyl, $C_1$–$C_6$ alkoxy, trifluoromethoxy, halogen, or cyano; and
W represents up to three substitutents independently chosen from $C_1$–$C_6$ alkyl, trifluoromethyl, $C_1$–$C_6$ alkoxy, trifluoromethoxy, halogen, hydroxy, amino, and cyano.

Also included in the invention are compounds of Formula II:

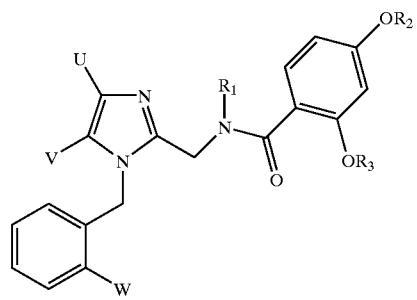

Formula II and the pharmaceutically acceptable salts thereof, wherein:
$R_1$, $R_2$ and $R_3$ are the same or different and independently represent $C_1$–$C_6$ alkyl;
U and V are the same or different and represent $C_1$–$C_4$ alkyl or halogen; and
W represents $C_1$–$C_4$ alkyl, trifluoromethyl, $C_1$–$C_4$ alkoxy, trifluoromethoxy, halogen, hydroxy, amino, or cyano.

Preferred compounds of Formula II include those where U and V are the same.

Other preferred compounds of Formula II are those where $R_2$ and $R_3$ are the same.

Still other preferred compounds of Formula II are those where $R_1$ is $C_4$–$C_5$ alkyl. Particular embodiments of the invention include compounds in which $R_1$ is butyl or methylbutyl, and most preferably 3-methylbutyl. Other preferred compounds of Formula II are those where $R_1$ is $C_4$–$C_5$ alkyl, especially butyl or methylbutyl, most preferably 3-methylbutyl, and U and V independently represent halogen or $C_1$–$C_3$ alkyl.

The invention further includes compounds of Formula II where $R_1$ is $C_4$–$C_5$ alkyl, preferably butyl or methylbutyl, most preferably 3-methylbutyl, and $R_2$ and $R_3$ independently represent $C_1$–$C_3$ alkyl. Particularly preferred are compounds of Formula II where $R_1$ is $C_4$–$C_5$ alkyl, $R_2$ and $R_3$ are independently $C_1$–$C_3$ alkyl, and U and V independently represent chloro, fluoro, or $C_1$–$C_3$ alkyl.

Other particularly preferred compounds of II are those where $R_1$ is $C_4$–$C_5$ alkyl, preferably butyl or methylbutyl, most preferably 3-methylbutyl, and W chloro, fluoro, $C_1$–$C_3$ alkyl, or trifluoromethyl. Still other preferred compounds of the invention are those where $R_1$ is $C_4$–$C_5$ alkyl, preferably butyl or methylbutyl, most preferably 3-methylbutyl, $R_2$ and $R_3$ are independently $C_1$–$C_3$ alkyl, U and V are the same or different and are chloro, fluoro or $C_1$–$C_3$ alkyl, and W is chloro, fluoro, $C_1$–$C_3$ alkyl, or trifluoromethyl.

The invention further includes a method for altering the signal-transducing activity of a cell surface GLP-1 receptor, said method comprising exposing cells expressing such a receptor to a solution containing a compound or salt of Formula I or Formula II, or any of the preferred embodiments of Formula II described above.

DETAILED DESCRIPTION OF THE INVENTION

Representative compounds of the present invention include, but are not limited to the compounds in Table 1 and their pharmaceutically acceptable acid addition salts. In addition, if the compound of the invention is obtained as an acid addition salt, the free base can be obtained by basifying a solution of the acid salt. Conversely, if a compound is obtained as a free base, an addition salt, preferably a pharmaceutically acceptable addition salt, may be produced by dissolving the free base in a suitable organic solvent and treating the solution with an acid, in accordance with conventional procedures for preparing acid addition salts from base compounds.

Preferred pharmaceutical salts are non-toxic, and include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, HOOC—$(CH_2)_n$—COOH where n is 0–4, and the like. Those skilled in the art will recognize a wide variety of non-toxic pharmaceutically acceptable addition salts.

The present invention also encompasses the prodrugs of the compounds of Formula I. Those skilled in the art will recognize various synthetic methodologies that may be employed to prepare non-toxic pharmaceutically acceptable prodrugs of the compounds encompassed by Formula I. Those skilled in the art will recognize a wide variety of non-toxic pharmaceutically acceptable solvates, such as water, ethanol, mineral oil, vegetable oil, and dimethylsulfoxide.

The GLP-1 receptor binding compounds provided by this invention and labeled derivatives thereof are also useful as standards and reagents in determining the ability of a potential pharmaceutical to bind to the GLP-1 receptor.

Labeled derivatives the GLP-1 receptor ligands provided by this invention are also useful as radiotracers for positron emission tomography (PET) imaging or for single photon emission computerized tomography (SPECT).

The present invention also pertains to methods for altering the activity of GLP-1 receptors, said method comprising exposing cells expressing such receptors to an effective amount of a compound of the invention, wherein the compound is present in the solution at a concentration sufficient to specifically alter the signal transduction activity of GLP-1 receptors in vitro. This method includes altering the signal transduction activity of GLP-1 receptors in vivo, e.g., in a patient given an amount of a compound of Formula I that would be sufficient to alter the signal transduction activity of cells expressing high levels of GLP-1 receptors in vitro. The amount of a compound that would be sufficient to alter the signal transduction activity of cells expressing GLP-1 receptors may be determined via an assay of GLP-1 receptor mediated signal transduction, such as an assay wherein the binding of GLP or a compound of the invention to a cell surface GLP-1 receptor effects a changes in reporter gene expression, e.g., in the firefly luciferase reporter gene assay of GLP-1 receptor modulation described above.

Representative compounds of the invention are shown in Table 1.

TABLE 1

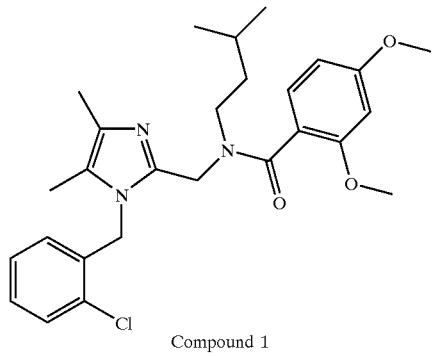

Compound 1

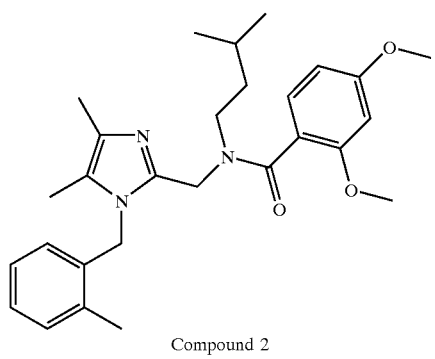

Compound 2

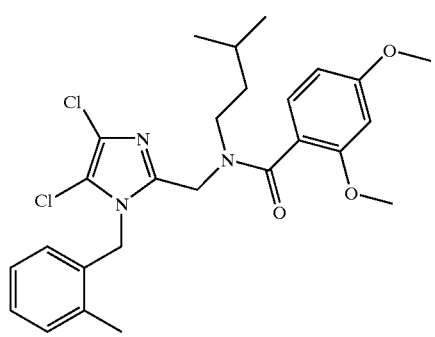

Compound 3

TABLE 1-continued

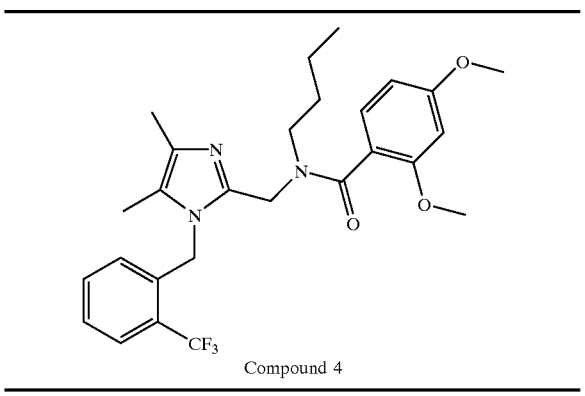

Compound 4

Definitions

Compounds that bind with "high affinity" are those that exhibit $K_i$ values of less than 1 uM, preferably exhibit $K_i$ values of less than 500 riM and most preferably those that exhibit $K_i$ values of less than 100 nM at cell surface receptors. Preferably, the cell surface receptors are GLP-1 receptors.

By "$C_1$–$C_6$ alkyl" or "lower alkyl" in the present invention is meant straight or branched chain alkyl groups having 1 to 6 carbon atoms, such as, for example, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl. Preferred lower alkyl groups are methyl, ethyl, propyl, and butyl.

By "$C_1$–$C_6$ alkoxy" or "lower alkoxy" in the present invention is meant straight or branched chain alkoxy groups having 1 to 6 carbon atoms, such as, for example, methoxy, ethoxy, propoxy, isopropoxy, n-butoxy, sec-butoxy, tert-butoxy, pentoxy, 2-pentyl, isopentoxy, neopentoxy, hexoxy, 2-hexoxy, 3-hexoxy, and 3-methylpentoxy. Preferred alkoxy groups herein are $C_1$–$C_4$ alkoxy groups.

By the term "halogen" in the present invention is meant fluorine, bromine, chlorine, and iodine.

Pharmaceutical Preparations

The compounds of general Formula I may be administered orally, topically, parenterally, by inhalation or spray or rectally in dosage unit formulations containing conventional non-toxic pharmaceutically acceptable carriers, adjuvants and vehicles. The term parenteral as used herein includes percutaneous, subcutaneous, intravascular (e.g., intravenous), intramuscular, or intrathecal injection or infusion techniques and the like. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants, and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preservative agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques. In some cases such coatings may be prepared by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropyl methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil or a mineral oil or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol, glucose or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be a sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds of general Formula I may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Compounds of general Formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

For administration to non-human animals, the composition may also be added to the animal feed or drinking water. It will be convenient to formulate these animal feed and drinking water compositions so that the animal takes in an appropriate quantity of the composition along with its diet. It will also be convenient to present the composition as a premix for addition to the feed or drinking water.

Frequency of dosage may also vary depending on the compound used and the particular disease treated. However, for treatment of most metabolic disorders including obesity and diabetes, a dosage regimen of 4 times daily or less is preferred. For the treatment of obesity a dosage regimen of 1 or 2 times daily is particularly preferred.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Preferred compounds of the invention will have certain pharmacological properties. Such properties include, but are not limited to oral bioavailability, low toxicity, low serum protein binding and desirable in vitro and in vivo half-lifes. Penetration of the blood brain barrier for compounds used to treat CNS disorders is necessary, while low brain levels of compounds used to treat periphereal disorders are often preferred.

Assays may be used to predict these desirable pharmacological properties. Assays used to predict bioavailability include transport across human intestinal cell monolayers, including Caco-2 cell monolayers. Toxicity to cultured hepatocyctes may be used to predict compound toxicity. Penetration of the blood brain barrier of a compound in humans may be predicted from the brain levels of the compound in laboratory animals given the compound intravenously.

Serum protein binding may be predicted from albumin binding assays. Such assays are described in a review by Oravcová, et al. (Journal of Chromatography B (1996) volume 677, pages 1–27).

Compound half-life is inversely proportional to the frequency of dosage of a compound. In vitro half-lives of compounds may be predicted from assays of microsomal half-life as described by Kuhnz and Gieschen (Drug Metabolism and Disposition, (1998) volume 26, pages 1120–1127).

The effect of a compound on blood glucose levels can be determined in vivo, through the use of a glucose tolerance test, in which the blood glucose levels laboratory animals subjected to a glucose challenge are monitored in the presence and absence of the compound. The effects of test compounds on glucose tolerance may be evaluated in non-diabetic laboratory animals as discussed in Wang et al., J. Clin. Invest. (1995) 95: 417–421 and Holst, *Curr. Opinion in Endocrinology and Diabetes* (1998) 5: 108–115. Alternatively, the effects of test compounds on blood glucose levels may be assessed in an animal model of diabetes, e.g., streptozotocin (STZ)-induced diabetes. Such assays have been disclosed by Tancrède et al. (Br. J. Exp. Path. (1983) 64: 117–123), Junod et al. (*J. Clin. Inv.* (1969) 48: 2129–2139, Rondu et al. (*J. Med. Chem.* (1997) 40:3793–3803), and Maloff and Boyd (*Diabetologia* (1986) 29: 295–300).

Chemical Synthesis

The compounds of the invention can be prepared using the chemical reactions depicted in Scheme 1. The starting materials for use in the various reactions may be varied to produce specific substitution patterns. Those skilled in the art will recognize the necessary variables.

The variables U, V, W, X, Y, Z, $R_1$, $R_2$ and $R_3$ in Scheme I are as defined for Formula I, and L is an appropriate leaving group such as, for example, halogen or sulfonate ester. Thus, an appropriately substituted imidazole 5 may be alkylated with an appropriately substituted benzyl halide or sulfonate ester in the presence of base to provide N-benzylated imidazole 6. This compound may then be subjected to the conditions of a Mannich reaction or similar conditions to produce 2-hydroxymethyl derivative 7. The hydroxy group of 7 may be converted into a leaving group, for instance by treatment with thionyl chloride or an alkylsulfonyl chloride to produce intermediate 8 which can be reacted with a primary amine under dilute conditions to give secondary amine 9. The amine may then be amidated to provide the compounds of Formula I.

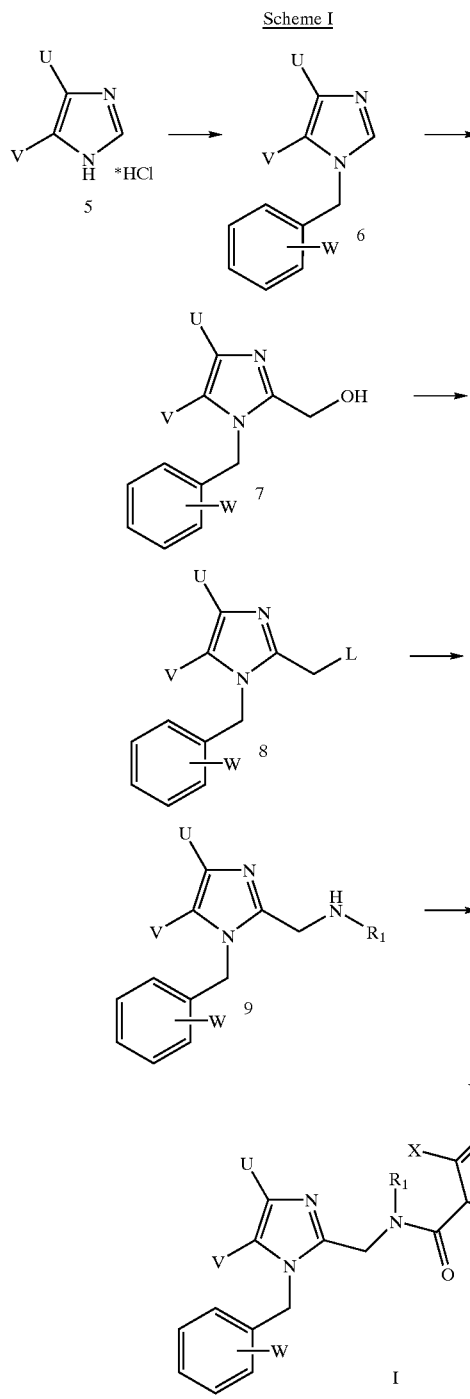

Scheme I

The invention is illustrated further by the following examples, which are not to be construed as limiting the invention in scope or spirit to the specific procedures and compounds described in them.

EXAMPLE 1

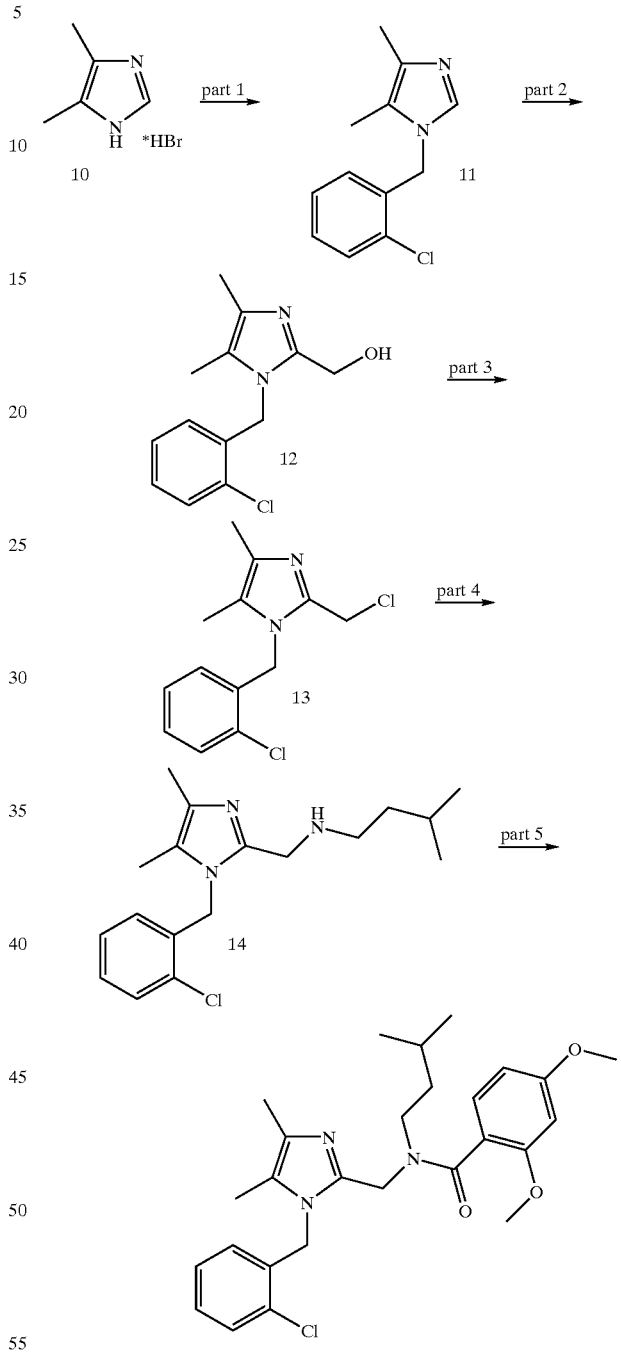

Scheme 2
Preparation of Compound 1

Compound 1

1. To a solution of 4.89 g (0.027 mol) of 4,5-dimethylimidazole hydrobromide and 5.7 g (0.028 mol) of 2-chlorobenzyl bromide in 20 ml of DMF is added 6 ml of 50% potassium hydroxide aqueous solution dropwise. The reaction mixture is stirred at room temperature under nitrogen overnight. The reaction mixture is then poured into ether (100 ml)/water (50 ml). The ether layer is separated, washed with water (10 ml×2), dried over anhydrous sodium sulfate and evaporated in vacuo. The raw material is subjected to chromatography on silica gel using dichloromethane-methanol (10:1) as eluant to give 2.67 g (0.012 mol, 44%) of 1-(2-chlorobenzyl)-4,5-dimethylimidazole as a pale yellow oil. LC-MS (M$^+$+1): 221.2; 1H-NMR (δ, CDCl$_3$): 2.00 (3H, s), 2.20 (3H, s), 5.07 (2H, s), 6.59 (1H, dd, J=9.2, 2), 7.17 (1H, td, J=8, 1.2), 7.23 (1H, td, J=8, 1.6), 7.38 (2H, dd, J=7.2, 1.6).

2. To a solution of 10 ml of glacial acetic acid and 10 ml of 37% formaldehyde is added 2.67 g (0.012 mol) of 1-(2'-chlorobenzyl)-4,5-dimethylimidazole. The mixture is stirred and heated in a sealed tube at 125–130° C. (oil bath temperature) overnight. After cooling, the solvent is evaporated in vacuo. The residue is subjected to chromatography on silica gel using dichloromethane-methanol (10:1) as eluant to give 2.39 g (9.5 mmol, 79%) of 1-(2-chlorobenzyl)-4,5-dimethyl-2-hydroxymethylimidazole as colorless powder. LC-MS (M$^+$+1): 251.1; 1H-NMR (δ, CDCl$_3$): 1.94 (3H, s), 2.11 (3H, s), 4.53 (2H, s), 5.26 (2H, s), 6.42 (1H, dd, J=8, 1.2), 7.14 (1H, td, J=8, 1.2), 7.21 (1H, td, J=7.4, 1.6), 7.39 (1H, dd, J=8, 1.2).

3. To 3 ml of thionyl chloride is added 2.39 g (9.5 mmol) of 1-(2-chlorobenzyl)-4,5 dimethyl-2-hydroxymethylimidazole. The mixture is heated at 50° C. for about 5 min., and the thionyl choride is evaporated in vacuo. The residue is then dissolved in 10 ml of dichloromethane, and subsequently evaporated in vacuo. This is repeated twice to give 1-(2-chlorobenzyl)-4,5-dimethyl-2-chloromethylimidazole (4) as a cream colored foam which is used without further purification.

4. To a solution of 7 ml (60 mmol) of isoamylamine in 3 ml of acetonitrile is added slowly a solution of 13 in 10 ml of acetonitrile followed by addition of 1.5 g (10.8 mmol) of potassium carbonate powder. The reaction mixture is stirred at room temperature overnight (under nitrogen), and excess isoamylamine is evaporated in vacuo. The residue is dissolved in 50 ml of ethyl acetate and 25 ml of water. The ethyl acetate layer is separated, washed with brine, dried over anhydrous sodium sulfate and evaporated in vacuo. The crude product is purified by preparative thin layer chromatography [silica gel, chloroform-methanol-ammonia hydroxide (90:10:1)] to give 1.39 g (4.4 mmol, 46%) of 14, 1-[(2-chlorobenzyl)-4,5-dimethylimidazol-2-yl]methyl (3-methylbutyl)amine, as a yellow oil. LC-MS (M$^+$+1): 320.2; 1H-NMR (δ, CDCl$_3$) : 0.81 (6H, d, J=6.4) , 1.25 (2H, m), 1.51 (1H, m), 1.96 (3H, s), 2.17 (3H, s), 2.56 (2H, m), 3.68 (2H, s), 5.21 (2H, s), 6.39 (1H, d, J=7.6), 7.13 (1H, m), 7.19 (1H, m), 7.37 (1H, m).

5. To a solution of 210 mg (0.66 mmol) of 14 in 5 ml of chloroform (stabilized with amylenes) is added 170 mg (0.84 mmol) of 2,4-dimethoxybenzoyl chloride and 1 ml of triethylamine. The reaction mixture is stirred at room temperature under nitrogen overnight and evaporated in vacuo. The resulting residue is dissolved in 20 ml of ethyl acetate and 10 ml of water. The ethyl acetate layer is separated, washed with brine (5 ml×2), dried over anhydrous. sodium sulfate, and the solvent evaporated in vacuo. The crude product is purified by preparative thin layer chromatography [silica gel, chloroform-methanol-ammonia hydoxide (95:4.5:0.5)] to give N-(3-methylbutyl)-2,4-dimethoxy-N-[[1-(2-chlorophenylmethyl)-4,5-dimethyl-1H-imidazol-2-yl]methyl]benzamide (Compound 1) as a colorless oil. LC-MS (M$^+$+1): 484.3; 1H-NMR (δ, CDCl$_3$) : 0.60 and 0.87 (6H, d, J=6, the ratio of two peaks is 4/1), 1.27 (2H, m), 1.57 (1H, m), 1.85 and 1.91 (3H, s, the ratio of two peaks is 1/4), 2.12 and 2.15 (3H, s, the ratio of two peaks is 1/4), 3.00 (2H, br), 3.66 and 3.71 (3H, s, the ratio of two peaks is 1/4), 3.69 and 3.73 (3H, s, the ratio of two peaks is 1/4), 4.61, 4.95, 5.18, 5.41 (4H, 4br), 6.25–6.36 (4H, m), 7.12 (1H, td, J=7.2, 1.2), 7.18 (1H, td, J=7.2, 1.2), 7.35 (1H. dd, J=8, 1.2).

The oil is dissolved in 5 ml of ether. 1 M HCl in ether is added dropwise to pH 2. The solvent is then evaporated in vacuo to give 200 mg (0.38 mmol, 58%) of the hydrochloride salt as a colorless foam.

EXAMPLE 2

The following compounds are prepared essentially according to the procedures set forth in Example 1 and outlined in Schemes 1 and 2, above.

(a) N-(3-methylbutyl)-2,4-dimethoxy-N-[[1-(2-methylphenylmethyl)-4,5 dimethyl-1H-imidazol-2-yl]methyl]benzamide (Compound 2).

LC-MS (M$^+$+1): 464.6;
$^1$H-NMR (δ, CDCl$_3$): 0.59 and 0.88 (6H, d, J=6.4, the ratio of two peaks is 4/1), 1.22 (2H, m), 1.34 (1H, br), 1.96 (3H, s), 2.18 (3H, s), 2.32 (3H, s), 2.93 (2H, t, J=7.2), 3.69 (3H, s), 3.72 (3H, s), 4.34, 4.94, 5.24 and 5.40 (4H, 4br), 5.73 (1H, d, J=8.8), 6.16 (1H, dd, J=8.2, 2), 6.22 (1H, d, J=&.2), 6.33 (1H, d, J=1.6), 7.06 (1H, m), 7.16 (2H, m).

(b) N-(3-methylbutyl)-2,4-dimethoxy-N-[[1-(2-methylphenylmethyl)-4,5 dichloro-1H-imidazol-2-yl]methyl]benzamide (Compound 3).

LC-MS (M$^+$+1): 506.2;
$^1$H-NMR (δ, CDCl$_3$) : 0.65 and 0.82 (6H, d, J=6.8, the ratio of two peaks is 9/1), 1.30 (3H, m), 2.37 and 2.38 (3H, s, the ratio of two peaks is 9/1), 3.05 (2H, t, J=7.6), 3.73 and 3.74 (3H, s, the ratio of two peaks is 9/1), 3.77 and 3.78 (3H, s, the ratio of two peaks is 9/1), 4.45, 5.03, 5.21 and 5.52 (4H, 4br), 5.94–6.40 (4H, m), 7.10–7.26 (3H, m).

(c) N-(4-Butyl)-2,4-dimethoxy-N-[[1-(2-trifluoromethylphenylmethyl)-4,5 dimethyl-1H-imidazol-2-yl]methyl]benzamide (Compound 4).

LC-MS (M$^+$+1): 518.2;
$^1$H-NMR (δ, CDCl$_3$): 0.62 and 0.89 (6H, d, J=6.4, the ratio of two peaks is 4/1), 1.31 (3H, m), 1.80 and 1.87 (3H, s, the ratio of two peaks is 1/4), 2.12 and 2.16 (3H, s, the ratio of two peaks is 1/4), 3.05 (2H, br), 3.67 and 3.72 (3H, s, the ratio of two peaks is 1/4), 3.70 and 3.75 (3H, s, the ratio of two peaks is 1/4), 4.58 (2H, br), 5.35 (1H, br), 5.53 (1H, br), 6.33 (1H, dd, J=8.4, 2.4), 6.38 (1H, d, J=2.4), 6.41 (1H, d, J=7.6), 6.57 (1H, d, J=8), 7.34 (1H, t, J=7.2), 7.41 (1H, t, J=7.2), 7.66 (1H, d, J=7.6).

(d) N-(3-methylbutyl)-2,4-dimethoxy-N-[[1-(2-chlorophenylmethyl)-4,5 dichloro-1H-imidazol-2-yl]methyl]benzamide (Compound 15).

LC-MS (M$^+$+1): 524.2, 526.0;
$^1$H-NMR (δ, CDCl$_3$): 0.65 and 0.90 (6H, d, J=6.6, the ratio of two peaks is 4/1), 1.32 (3H, m), 3.11 (2H, t, J=7.6), 3.74 (3H, s), 3.77 (3H, s), 4.73 and 5.50 (4H, 2br), 6.36 (1H, dd, J=8.4, 2.4), 6.40 (1H, d, J=2.4), 6.43 (1H, d, J=7.6), 6.58 (1H, d, J=7.6), 7.17–7.27 (2H, m), 7.41 (1H, dd, J=8, 1.2).

(e) N-(3-methylbutyl)-2,4-dimethoxy-N-[[1-(2-trifluoromethylphenylmethyl)-4,5 dimethyl-1H-imidazol-2-yl]methyl]benzamide (Compound 16).

EXAMPLE 3

Glucose Tolerance Test

Following overnight fasting adult male (200–300 g) Sprague-Dawley rats are injected orally with either vehicle or a glucose and vehicle solution in a given concentration. Following thirty-five minutes of resting in their home cages, the animals are brought back into the laboratory and restrained using a BRAINTREE SCIENTIFIC adjustable restrainer. Within five minutes of restraint, one of the lateral tail veins is catheterized, and the animals are given intravenous (iv) injection of either glucagon-like polypeptide 1 (GLP1) or test compound. Animals used for negative control are do not receive GLP1 or test compound. Five minutes after iv injection, the animals are euthanized by decapitation, and trunk blood is collected in tubes containing EDTA. The plasma levels of insulin and glucose measured using appropriate radio-immunoassay (RIA) kits. Administration of preferred compounds of the invention results in plasma glucose levels that are significantly less (at the p<0.05 level of significance) than those observed in animals treated only with glucose and vehicle.

EXAMPLE 4

Streptozocin-Induced Diabetes Glucose Tolerance Test

Streptozotocin (STZ) is an antibiotic extracted from *Streptomyces achromogenes*, which when injected into animals, causes pancreatic β-cell degranulation and necrosis. To achieve mild necrosis of pancreatic β-cells, which induces a state of diabetes without affecting normal development and weight gain, a 35 mg/kg/5 ml dose STZ is injected intraperitoneally (ip) into a group of healthy, naive animals. A control group of animals receive 0.1 N citrate buffer (vehicle, 5 ml/kg, 10=16). Five days after ip injections (day 5), diabetic symptoms are assessed via the following test of glucose tolerance. All animals receive an oral injection of 3g/kg/loml glucose solution between 3:00 and 5:00 PM. Forty minutes later, animals are restrained, a blood sample is taken from a lateral tail vein, and blood glucose levels are measured using the LIFE SCAN ONE TOUCH glucose monitoring system. Animals with blood glucose levels that are 100 to 250% higher than non-STZ treated animals (typically achieved in ⅔ of the STZ-treated animals) are considered STZ diabetic animals.

To assess the effect of a compound of Formula I on blood sugar levels in this animal model of diabetes, the compound is injected iv or orally into STZ diabetic animals on day 7, following overnight fasting, and glucose tolerance testing is carried out at intervals. In such studies, IV injection of GLP-1 is used as a positive control. Injection of preferred compounds of the invention results in blood glucose levels in STZ diabetic rats forty minutes after glucose injection of less than 200 mg/dl.

EXAMPLE 5

Preparation of Radiolabeled Probe Compounds of the Invention

The compounds of the invention are prepared as radiolabeled probes by carrying out their synthesis using precursors comprising at least one atom that is a radioisotope. The radioisotope is preferably selected from of at least one of carbon (preferably $^{14}C$), hydrogen (preferably $^3H$), sulfur (preferably 35S), or iodine (preferably 125I). Such radiolabeled probes are conveniently synthesized by a radioisotope supplier specializing in custom synthesis of radiolabeled probe compounds. Such suppliers include Amersham Corporation, Arlington Heights, Ill.; Cambridge Isotope Laboratories, Inc. Andover, Mass.; SRI International, Menlo Park, Calif.; Wizard Laboratories, West Sacramento, Calif.; ChemSyn Laboratories, Lexena, Kan.; American Radiolabeled Chemicals, Inc., St. Louis, Mo.; and Moravek Biochemicals Inc., Brea, Calif.

Tritium labeled probe compounds are also conveniently prepared catalytically via platinum-catalyzed exchange in tritiated acetic acid, acid-catalyzed exchange in tritiated trifluoroacetic acid, or heterogeneous-catalyzed exchange with tritium gas. Such preparations are also conveniently carried out as a custom radiolabeling by any of the suppliers listed in the preceding paragraph using the compound of the invention as substrate. In addition, certain precursors may be subjected to tritium-halogen exchange with tritium gas, tritium gas reduction of unsaturated bonds, or reduction using sodium borotritide, as appropriate.

EXAMPLE 6

Receptor Autoradiography

Receptor autoradiography (receptor mapping) is carried out in vitro as described by Kuhar in sections 8.1.1 to 8.1.9 of Current Protocols in Pharmacology (1998) John Wiley & Sons, New York, using radiolabeled compounds of the invention prepared as described in the preceding Example.

EXAMPLE 7

Additional Aspects of the Invention Additional Aspects of Preferred Compounds of the Invention The most preferred compounds of the invention are suitable for pharmaceutical use in treating human patients. Accordingly, such preferred compounds are non-toxic. They do not exhibit single or multiple dose acute or long-term toxicity, mutagenicity (e.g., as determined in a bacterial reverse mutation assay such as an Ames test), teratogenicity, tumorogenicity, or the like, and rarely trigger adverse effects (side effects) when administered at therapeutically effective dosages.

Preferably, administration of such preferred compounds of the invention at certain doses (e.g., doses yielding therapeutically effective in vivo concentrations or preferably doses of 10, 50, 100, 150, or 200 mg/kg—preferably 150 mg/kg—administered parenterally or preferably orally) does not result in prolongation of heart QT intervals (i.e., as determined by electrocardiography, e.g., in guinea pigs, minipigs or dogs). When administered daily for 5 or preferably ten days, such doses of such preferred compounds also do not cause liver enlargement resulting in an increase of liver to body weight ratio of more than 100%, preferably not more than 75% and more preferably not more than 50% over matched controls in laboratory rodents (e.g., mice or rats). In another aspect such doses of such preferred compounds also preferably do not cause liver enlargement resulting in an increase of liver to body weight ratio of more than 50%, preferably not more than 25%, and more preferably not more than 10% over matched untreated controls in dogs or other non-rodent animals.

In yet another aspect such doses of such preferred compounds also preferably do not promote the release of liver enzymes (e.g., ALT, LDH, or AST) from hepatocytes in vivo. Preferably such doses do not elevate such enzymes by more than 100%, preferably not by more than 75% and more preferably not by more than 50% over matched untreated controls in laboratory rodents. Similarly, concentrations (in culture media or other such solutions that are contacted and incubated with cells in vitro) equivalent to two, fold, preferably five-fold, and most preferably ten-fold the minimum in vivo therapeutic concentration do not cause release of any of such liver enzymes from hepatocytes in vitro.

Because side effects are often due to undesirable receptor activation or antagonism, particularly preferred compounds of the invention exert their receptor-modulatory effects with high selectivity. This means that they do not bind to certain other receptors (i.e., other than GLP1 receptors) with high affinity, but rather only bind to, activate, or inhibit the activity of such other receptors with affinity constants of greater than 100 nanomolar, preferably greater than 1 micromolar, more preferably greater than 10 micromolar and most preferably greater than 100 micromolar. Such receptors preferably are selected from the group including ion channel receptors, including sodium ion channel receptors, neurotransmitter receptors such as alpha- and beta-adrenergic receptors, muscarinic receptors (particularly m1, m2, and m3 receptors), dopamine receptors, and metabotropic glutamate receptors; and also include histamine receptors and cytokine receptors, e.g., interleukin receptors, particularly IL-8 receptors. The group of other receptors to which preferred compounds do not bind with high affinity includes $GABA_A$ receptors, bioactive peptide receptors (including NPY and VIP receptors), neurokinin receptors, and bradykinin receptors (e.g., BK1 receptors and BK2 receptors).

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A compound of the formula:

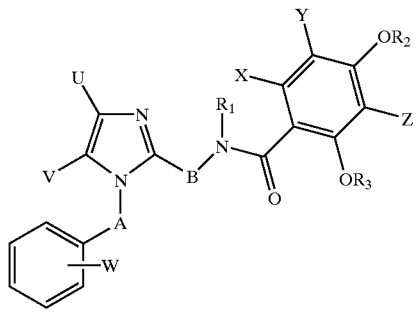

or a pharmaceutically acceptable salt thereof, wherein:
A and B are independently $C_1$–$C_3$ alkylene;
$R_1$ is $C_1$–$C_6$ alkyl;
$R_2$ and $R_3$ are the same or different and represent hydrogen or $C_1$–$C_6$ alkyl;
U and V are the same or different and represent $C_1$–$C_6$ alkyl or halogen;
X, Y and Z are the same or different and represent hydrogen, $C_1$–$C_6$ alkyl, trifluoromethyl, $C_1$–$C_6$ alkoxy, trifluoromethoxy, halogen, or cyano; and
W represents up to three substitutents independently chosen from $C_1$–$C_6$ alkyl, trifluoromethyl, $C_1$–$C_6$ alkoxy, trifluoromethoxy, halogen, hydroxy, amino, and cyano.

2. A compound of the formula:

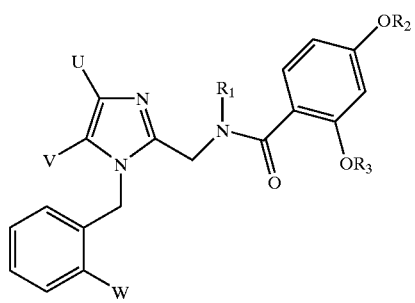

or a pharmaceutically acceptable salt thereof, wherein:
$R_1$, $R_2$ and $R_3$ are the same or different and represent $C_1$–$C_6$ alkyl;
U and V are the same or different and represent $C_1$–$C_4$ alkyl or halogen;
W represents $C_1$–$C_4$ alkyl, trifluoromethyl, $C_1$–$C_4$ alkoxy, trifluoromethoxy, halogen, hydroxy, amino, or cyano.

3. A compound or salt according to claim 2, wherein U and V are the same.

4. A compound or salt according to claim 2, wherein $R_2$ and $R_3$ are the same.

5. A compound or salt according to claim 2, wherein $R_1$ is $C_4$–$C_5$ alkyl.

6. A compound or salt according to claim 5, wherein U and V independently represent halogen or $C_1$–$C_3$ alkyl.

7. A compound or salt according to claim 5, wherein $R_2$ and $R_3$ independently represent $C_1$–$C_3$ alkyl.

8. A compound or salt according to claim 7, wherein U and V independently represent chloro, fluoro, or $C_1$–$C_3$ alkyl.

9. A compound or salt according to claim 5, wherein W is chloro, fluoro, $C_1$–$C_3$alkyl, or trifluoromethyl.

10. A compound or salt according to claim 8, wherein W is chloro, fluoro, $C_1$–$C_3$alkyl, or trifluoromethyl.

11. A compound or salt according to claim 1, which is N-(3-methylbutyl)-2,4-dimethoxy-N-[[1-(2-methylphenylmethyl)-4,5 dimethyl-1H-imidazol-2-yl]methyl]benzamide.

12. A compound or salt according to claim 1, which is N-(3-methylbutyl)-2,4-dimethoxy-N-[[1-(2-methylphenylmethyl)-4,5-dichloro-1H-imidazol-2-yl]methyl]benzamide.

13. A compound or salt according to claim 1, which is N-(4-Butyl)-2,4-dimethoxy-N-[[1-(2-trifluoromethylphenylmethyl)-4,5 dimethyl-1H-imidazol-2-yl]methyl]benzamide.

14. A compound or salt according to claim 1, which is N-(3-methylbutyl)-2,4-dimethoxy-N-[[1-(2-chlorophenylmethyl)-4,5-dimethyl-1H-imidazol-2-yl]methyl]benzamide.

15. A compound or salt according to claim 1, which is N-(3-methylbutyl)-2,4-dimethoxy-N-[[1-(2-chlorophenylmethyl)-4,5-dichloro-1H-imidazol-2-yl]methyl]benzamide.

16. A compound or salt according to claim 1, which is N-(3-methylbutyl)-2,4-dimethoxy-N-[[1-(2-trifluoromethylphenylmethyl)-4,5dimethyl-1H-imidazol-2-yl]methyl]benzamide.

17. A method of treating diabetes, comprising administering to a patient in need of such treatment a therapeutically effective amount of a compound or salt according to claim 1.

18. A method of treating obesity or eating disorders, comprising administering to a patient in need of such treatment a therapeutically effective amount of a compound or salt according to claim 1.

19. A pharmaceutical composition comprising a compound or salt according to claim 1 and a pharmaceutically acceptable carrier.

20. A packaged pharmaceutical composition comprising a pharmaceutical composition of claim 19 in a container and instructions for using the composition to treat a patient suffering from diabetes.

21. A packaged pharmaceutical composition comprising a pharmaceutical composition of claim 19 in a container and instructions for using the composition to treat a patient suffering from obesity or instructions for using the composition to treat a patient suffering from an eating disorder.

22. A method for detecting GLP-1 receptors in tissue samples comprising:

contacting with a sample of tissue a compound or salt according to claim 1 which has been detectably labeled, said contacting being carried out under conditions that permit binding of the compound or salt to any GLP-1 receptors within the sample of tissue, washing the tissue sample to remove unbound compound, and detecting the remaining bound compound, wherein the detection of the remaining bound compound is an indication of the presence of GLP-1 receptors in the sample of tissue.

\* \* \* \* \*